United States Patent [19]

Rosenblatt

[11] Patent Number: 4,950,247
[45] Date of Patent: * Aug. 21, 1990

[54] ASPIRATOR FOR COLLECTION OF BODILY FLUIDS INCLUDING IMPROVED SAFETY AND EFFICIENCY ELEMENTS

[75] Inventor: Richard Rosenblatt, Beverly Hills, Calif.

[73] Assignee: Rosenblatt/IMA Invention Enterprises, Beverly Hills, Calif.

[ * ] Notice: The portion of the term of this patent subsequent to Oct. 3, 2005 has been disclaimed.

[21] Appl. No.: 209,852

[22] Filed: Jun. 22, 1988

Related U.S. Application Data

[63] Continuation-in-part of Ser. No. 903,017, Sep. 2, 1986, Pat. No. 4,775,366.

[51] Int. Cl.$^5$ ............................................... A61M 5/00
[52] U.S. Cl. .................................... 604/181; 604/216; 604/319; 128/767; 128/768; 128/202.29
[58] Field of Search ............... 604/128, 129, 215, 216, 604/217, 250, 264, 319, 902, 73, 76, 118, 119, 133, 181, 183, 185, 212, 275, 276, 313, 317, 318; 128/760, 767, 768, 201.25, 202.28, 202.29, 203.11

[56] References Cited

U.S. PATENT DOCUMENTS

| | | |
|---|---|---|
| 869,262 | 10/1907 | Pynchon . |
| 3,084,691 | 4/1963 | Stoner . |
| 3,626,928 | 12/1971 | Hohokus . |
| 3,636,940 | 1/1972 | Gravlee . |
| 3,830,238 | 8/1974 | Kurtz . |
| 3,855,997 | 12/1974 | Sauer .................................. 604/319 |
| 3,875,941 | 4/1975 | Adair .................................. 604/133 |
| 3,892,226 | 7/1975 | Rosen . |
| 4,228,798 | 10/1980 | Deaton .................................. 604/49 |
| 4,317,525 | 3/1982 | Schuessler . |
| 4,430,084 | 2/1984 | Deaton .................................. 604/319 |
| 4,460,354 | 7/1984 | Weilbacher . |
| 4,468,226 | 8/1984 | Kurtz . |
| 4,487,606 | 12/1984 | Leviton et al. ...................... 604/319 |
| 4,534,542 | 8/1985 | Russo .................................. 604/119 |
| 4,578,060 | 3/1985 | Huck et al. ......................... 604/133 |
| 4,642,093 | 2/1985 | Härle .................................. 604/54 |
| 4,715,856 | 12/1987 | Elliot et al. ......................... 604/319 |
| 4,775,366 | 10/1988 | Rosenblatt ...................... 128/202.29 |

FOREIGN PATENT DOCUMENTS 698616 11/1979 U.S.S.R. .

Primary Examiner—John D. Yasko
Assistant Examiner—Anthony M. Gutowski
Attorney, Agent, or Firm—Thomas I. Rozsa

[57] ABSTRACT

An aspirator including a container having two separate chambers with one chamber having a suction tube connected to a closed bellows within the chamber for creating a vacuum, and the second chamber having a patient tube for insertion into the body cavity of a patient for sucking removal of mucus and other excess bodily fluids by the vacuum, with the two containers being connected for gaseous communication. The aspirator further includes an injection port by which mucus may be removed from the container and a pressure relief valve to permit air to escape from the container as the flexible bellows expands to its equilibrium state. The suction tube further includes a moisture trap to occlude gaseous flow to the mouthpiece in the event moisture enters the suction system. The apparatus further includes a clip to occlude fluid flow through the patient tube when the operation is completed. The patient tube may include a Yankauer tip. The bellows cap may be attached to the underside of the top of the container in one of several ways.

21 Claims, 4 Drawing Sheets

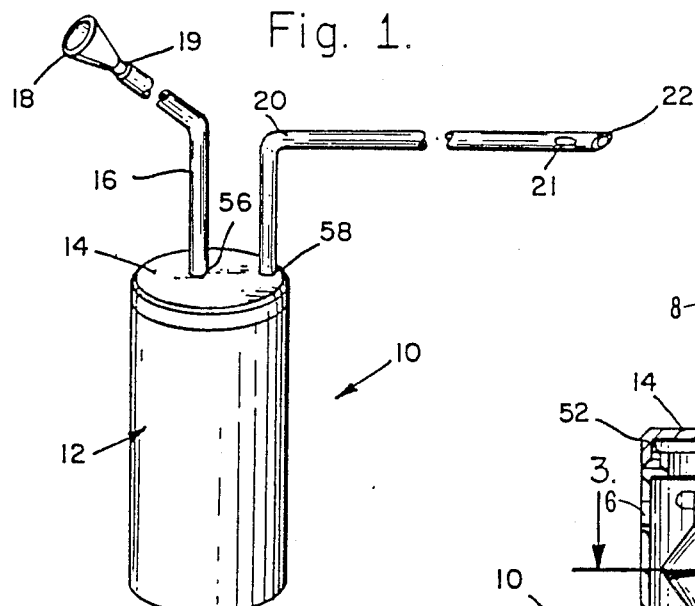
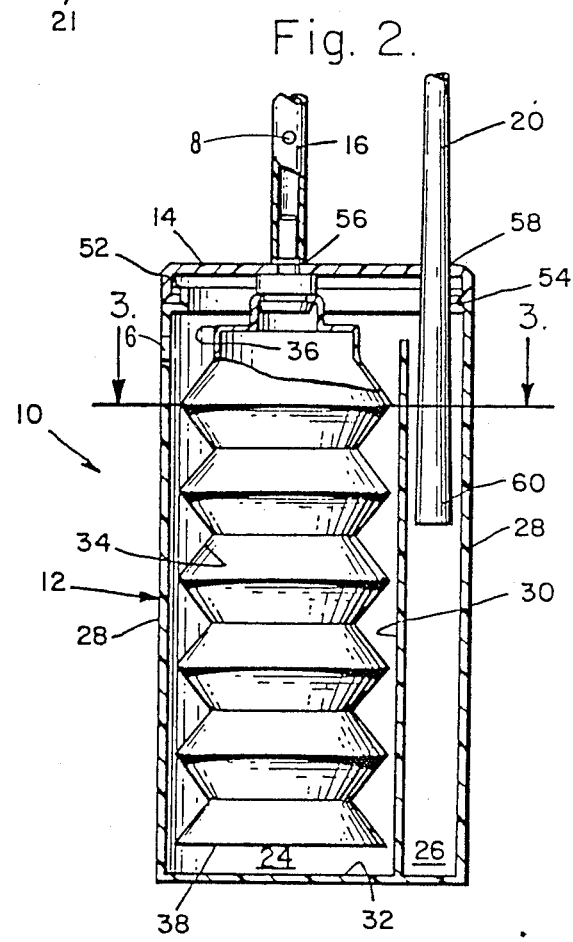
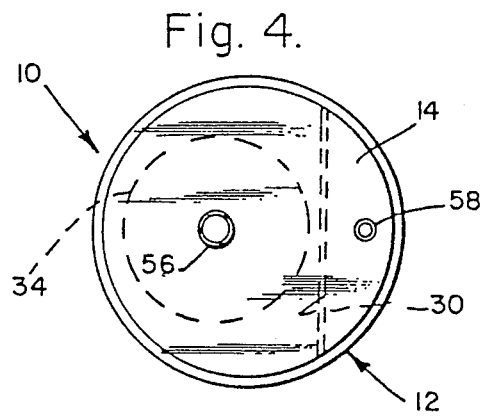
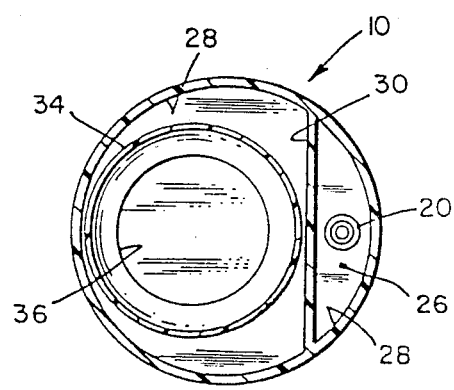
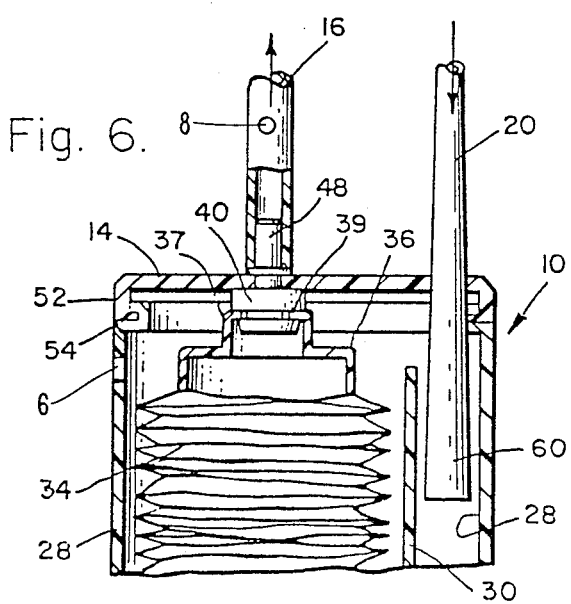

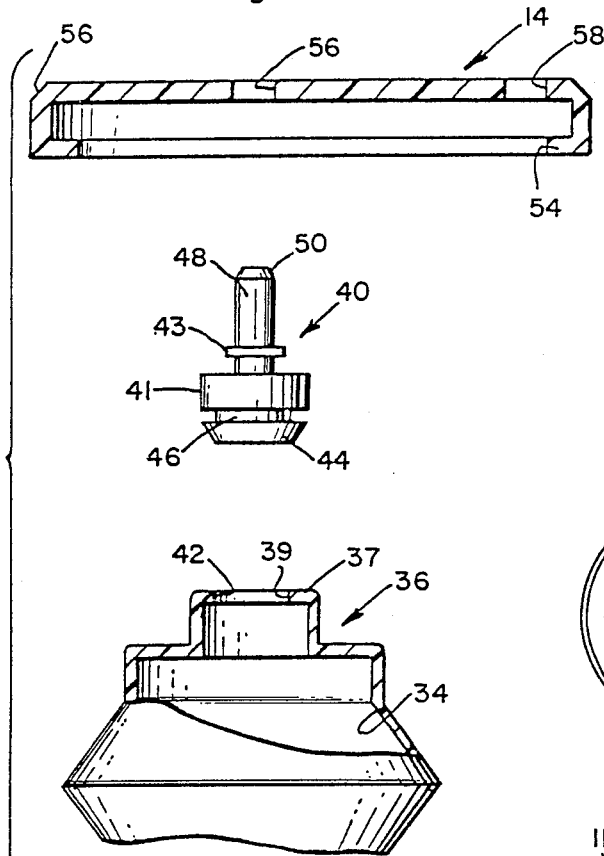
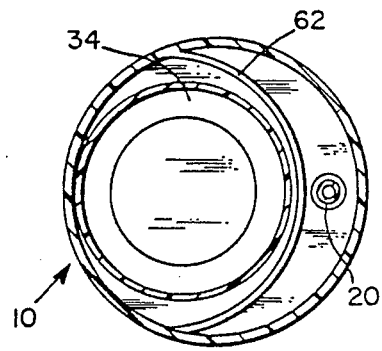
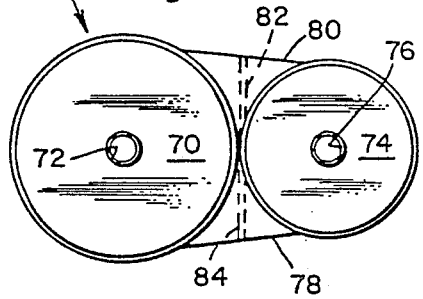
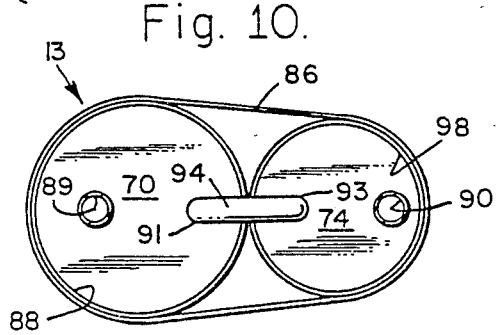
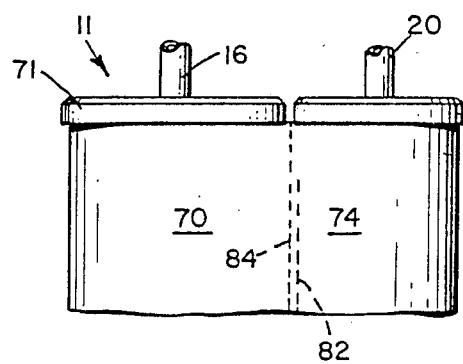
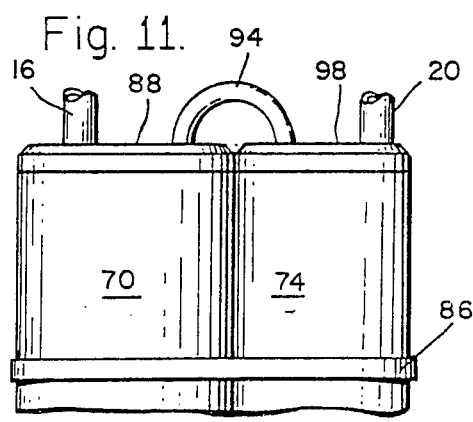
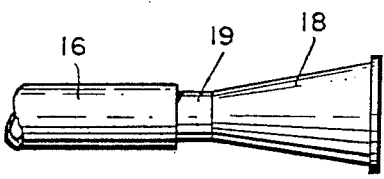

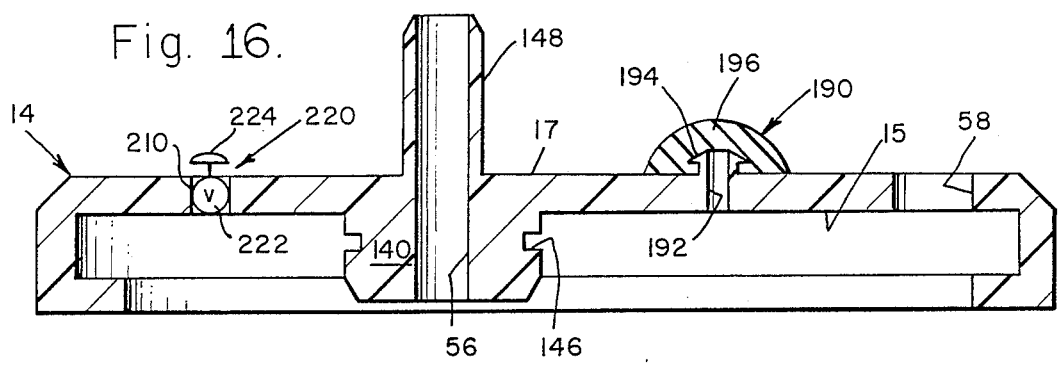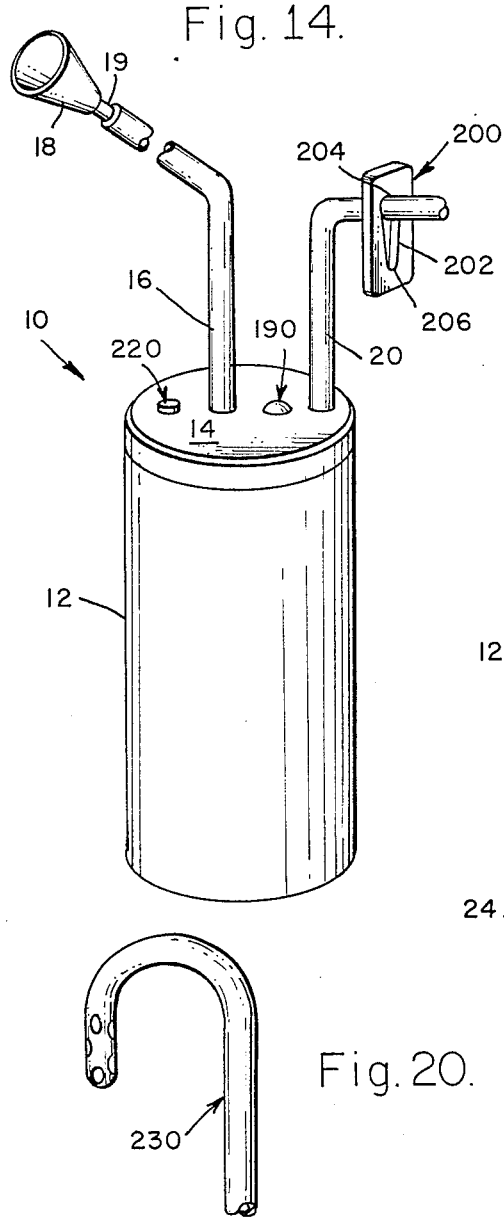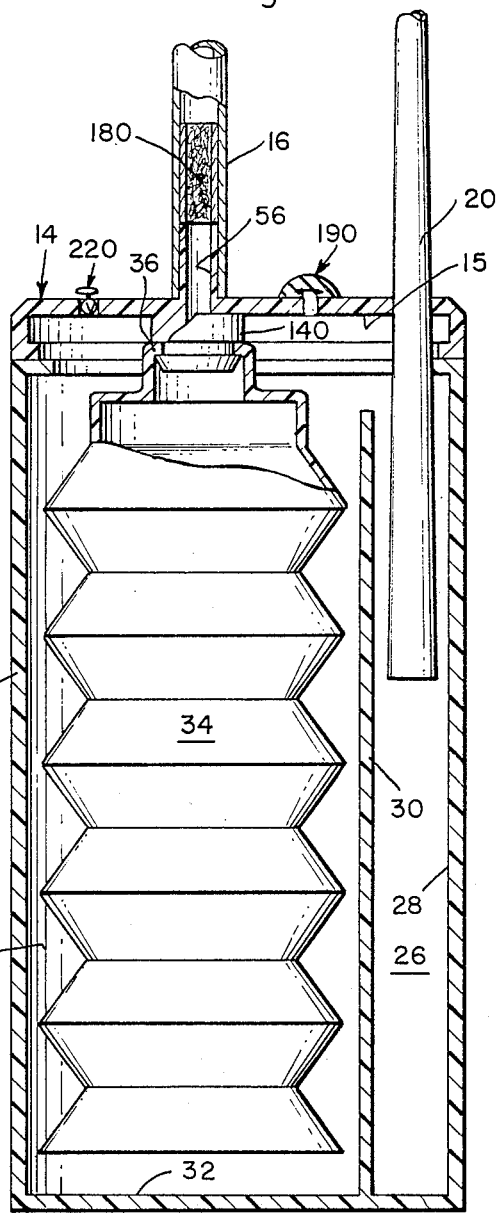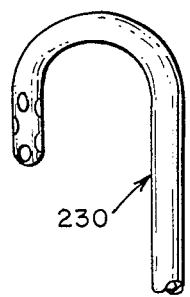

4,950,247

ASPIRATOR FOR COLLECTION OF BODILY FLUIDS INCLUDING IMPROVED SAFETY AND EFFICIENCY ELEMENTS

This application is a Continuation-In-Part Application of co-pending Application Ser. No. 903,017 filed on Sept. 2, 1986, now U.S. Pat. No. 4,775,366.

1. FIELD OF THE INVENTION

The present invention relates to aspirators. More particularly, the present invention relates to an aspirator for removing bodily fluid from a body cavity, such as mucus from the mouth and throat, through oral suction by another person.

2. DESCRIPTION OF THE PRIOR ART

It is often necessary to remove bodily fluids, such as mucus and other matter, from the throat of a patient, especially in the case of newborn infants. Vacuum operated collection devices for collecting such bodily fluids are known in prior art.

Such collection devices generally include a container having a screw-on or snap-on cap that provides a fluid-tight closure, and a pair of tubes connected to nipples protruding from the cap in fluid communication with the interior of the container and with each other. In use, one of the tubes is connected to a source of vacuum or a suction force, for example, a mouthpiece for providing suction by mouth, or to another conventional source of hospital vacuum. The other tube may be inserted into the throat or other body cavity of the patient to permit withdrawal of fluid from the bodily cavity, and its collection in the container, in response to suction.

An example of this type of fluid collection device is found in U.S. Pat. No. 4,317,525, issued to Schuessler et al., which includes the improvement of including a weak portion in the wall adjacent the cap to facilitate removal of the cap. Such devices, however, allow air from the patient's body cavity to enter the suction tube, where bacteria or germs in it can contaminate and infect either a person who is sucking, or a hospital suction system.

Another such fluid collection system is disclosed in U.S. Pat. No. 3,084,691, to Stoner. Stoner includes a foot-operated bellows pump for creating suction in a collection chamber having two nipples and mating tubes attached thereto, with one of the nozzles being used to suck bodily fluids from a body cavity. The apparatus in Stoner is relatively large, bulky, complex and expensive. In addition, it does not provide any indication of the amount of resistance to the sucking, which provides important feedback to a person using the device, who can responsively apply only the suction necessary to remove the subject liquids. Finally, Stoner too allows communication of the air to the nurse from the patient through the pump.

While the prior art discloses bodily fluid collection devices relying on suction, such devices allow communication of air, and other gas from the patient through the device, and in the instance of a manually operated device, into the nurse or other health care provider. Although such devices do not normally allow liquid from the patient to enter into the suction system, they do allow air or other gas to enter into the suction tube and the source of vacuum, thereby increasing the danger of further spreading of communicable diseases.

Therefore, there is a significant need for a bodily fluid collection device that isolates both the liquid and the gas fluids extracted from a patient by the health care provider, through a suction apparatus.

SUMMARY OF THE INVENTION

Accordingly, it is an object of the present invention to provide a bodily fluid collection device that completely isolates gaseous and liquid fluids collected from the patient from the source of suction, which may conveniently be a person, such as a nurse.

It is a further object of the present invention to provide a bodily fluid collection device that is disposable.

It is a further object of the present invention to provide a bodily fluid collection device that is relatively inexpensive to manufacture.

It is a further object of the present invention to provide a bodily fluid collection device that is easy to open, thereby making the contents readily available for analysis.

It is a further object of the present invention to provide a disposable bodily fluid collection device that is sterile prior to use.

It is another object of the present invention to provide a bodily fluid collection device with several enhancements to aid in the efficiency and safety of operation, such as a moisture trap to prevent fluid from accidentally being sucked in by a person using the present invention to treat a patient, a pressure relief valve to depressurize the container as the bellows expand to its equilibrium state to thereby prevent air from being forced back through the patient tube and into the patient's stomach, an injection port by which the mucus may be withdrawn by a laboratory technician through use of a syringe so that the cap need not be opened and the risk of infection through direct contact with the mucus eliminated, and a clip to occlude air or liquid flow through the patient tube after the sucking operation has been completed.

It is a further object of the present invention to also enable the invention to be used in battlefield conditions to suck mucus and other fluids out of the mouths of wounded soldiers. By fitting the patient tube with an interchangeable Yankauer tip, the same aspirator of the present invention can be used over and over again by replacing the Yankauer tip when a new wounded soldier is worked on.

Accordingly, there is provided a container having a bottom wall and a sidewall, a top having two apertures therein, or the equivalent, such as two protruding nipples, removably attached to the container, a patient tube inserted through one of the apertures for insertion into a patient's body cavity, and a suction tube attached through the other aperture and having its remote end attached to a source of suction, which may be a person, or another conventional source of vacuum, and a means for transmitting a partial vacuum throughout the container and the patient tube without allowing fluid, that is, either gas or liquid, communication between the two tubes.

In a preferred embodiment, the vacuum transmitting means comprises a bellows that is expanded in its equilibrium or relaxed state, and that contracts in response to negative pressure, that is, in response to sucking on the suction tube, the suction tube being operatively connected to the bellows. In the preferred embodiment, the bellows is contained entirely within the container.

The invention may also include means for releasing air from the container during the relaxation cycle of the bellows, that is, means for permitting air to be exhausted from the container while the bellows expand without having the displaced air exhausted through the patient tube. This air releasing means may further comprise an aperture (6 as illustrated in FIG. 6) in the sidewall of the container, or in the sucking tube (aperture 8 as illustrated in FIG. 6) which is covered (for example by the operator) during sucking, and uncovered while the bellows is being restored to its equilibrium, that is, fully opened position. Alternatively, this air releasing means may be a spring loaded valve fit inside an aperture in the sidewall or top of the container. The valve is normally closed so no air can enter the container or escape from the container through this aperture. When a push button or similar release mechanism connected to the valve is activated, the valve opens to let air escape from the chamber, thereby depressurizing the entire container so the bellows can expand to its equilibrium position much more rapidly without the possibility of air or liquid being pushed up the patient tube and back into the patient's stomach.

Alternatively, the air releasing means may be automatic, and may include, for example, a ball valve seat disposed in the patient tube, preferably in the end of the patient tube that is contained within the container, the ball valve being forced closed during the relaxation or expansion cycle of the bellows, and drawn open during sucking, and a flap valve in the container, with the flap vale being naturally in the closed position during expansion of the bellows into its equilibrium position. Such air releasing means is not, however, necessary for proper and efficacious operation of the invention and may be too expensive for mass production of disposable aspirators.

Another feature of the preferred embodiment of the invention comprises an upstanding partition within the container, which is contiguous with the sidewall of the container along two lines and along the bottom wall, forming two chambers, which are a liquid collection chamber and a vacuum transmitting chamber, wherein said chambers are in gaseous communication, but not in liquid communication, because the upstanding partition does not extend to the top of the container. Plastic is a preferred material for making the container, the top and the nipple in the top for attaching the suction tube to the container. A nipple in the top of the container may also be used for attaching of the patient tube.

In a preferred embodiment, the container is cylindrical. The upstanding partition may be either straight, or arcuate. An arcuate upstanding partition is preferred because its use allows more efficient use of the space available within the container.

Another enhancement for safer utilization of the present invention is to provide a moisture trap inside the suction tube which acts as a moisture block. The moisture trap is a filter which permits air to pass when it is dry but if moisture is present, the filter swells up and occludes the passageway, preventing air from passing. This is a valuable safety enhancement in the event the bellows or other sealing arrangement should break and moisture from the sucked contents of the baby's stomach enter the suction system. By providing this occlusion, the possibility of the person working the apparatus sucking in such material or sucking in contaminated air is significantly reduced.

A further enhancement for more efficient operation of the present invention is the inclusion of an injection port located in the area where mucus is collected, for example in the cap immediately above the mucus trap area of the present invention aspirator. The injection portion includes an opening having a structural support member which supports a diaphragm. After the mucus is collected, instead of opening the cap to remove the mucus, the laboratory technician can place the needle of a syringe through the membrane and draw out the mucus into the syringe, thereby eliminating the possibility of coming in direct contact with contaminated mucus.

An additional enhancement is the inclusion of a clip on the patient tube to occlude flow of air or liquid after the suction process is completed, thereby further assuring that no mucus can flow out of the suction tube.

An additional improvement in the present invention is to include a Yankauer suction tip at the end of the patient tube so that the apparatus may be switched from patient to patient by replacement of the Yankauer tip. This is especially useful in battlefield conditions where the present invention aspirator may be used to remove mucus and other debris from the mouth of a wounded soldier. Due to the extreme conditions of battle, it is easier to maintain the same apparatus and merely switch suction tips when treating many different wounded soldiers.

Other alternative embodiments utilize two separate containers, one for containing the bellows, and the other for collecting the bodily fluid, and a means for conducting gas from one container to another. Such means may include an externally disposed flexible tube connected to the top of each container, or an internal partition. In either case, the bodily fluid collection chamber is readily detachable from the vacuum generating chamber, for permitting easy access to the collected liquid, for medical testing.

Further novel features and other objects of the present invention will become apparent from the following detailed description, discussion, and the appended claims taken in conjunction with the drawings.

BRIEF DESCRIPTION OF THE DRAWINGS

Referring particularly to the drawings for the purpose of illustration only and not limitation, there is illustrated:

FIG. 1 is a perspective view of an aspirator according to the present invention.

FIG. 2 is a section elevation of an aspirator according to the present invention, illustrating the bellows in their relaxed, or equilibrium position.

FIG. 3 is a section of an aspirator according to the present invention, taken along lines 3—3 of FIG. 2.

FIG. 4 is a plan view of an aspirator according to the present invention, without the tubes attached to the top.

FIG. 5 is a section of a aspirator according to the present invention, corresponding to FIG. 3, but showing an aspirator having an arcuate internal upstanding partition.

FIG. 6 is a partial cross-sectional elevation of an aspirator according to the present invention illustrating the bellows in their contracted, that is vacuum-creating state.

FIG. 7 is an exploded side elevation, partially fragmentary, illustrating the cap, bellows, and suction tube fitting for the vacuum-creating portion of the apparatus.

FIG. 8 is a plan view of an alternative embodiment of an aspirator according to the present invention in which separate circular containers are employed.

FIG. 9 is a fragmentary elevation of the apparatus of FIG. 8.

FIG. 10 is a plan view of an alternative embodiment of an aspirator according to the present invention in which separate circular containers are employed, and are joined in gaseous communication by an external tube that penetrates the top of each container.

FIG. 11 is a fragmentary elevational view of the apparatus of FIG. 10.

FIG. 12 is a fragmentary elevational of the suction tube according to the present invention, including the mouthpiece.

FIG. 13 is an elevation of the patient tube adapted for use with the present invention, illustrating the uniform taper that lodges the patient tube into correct position within the aspirator, and the Murphy tip at the remote end for insertion into the body cavity to be drained.

FIG. 14 is a perspective view of an aspirator according to the present invention, including several improvements for safer and more efficient operation.

FIG. 15 is a section elevation of an aspirator according to the present invention with improvements shown in FIG. 14, illustrating the bellows in their relaxed, or equilibrium position.

FIG. 16 is an enlarged view of the cap of the aspirator with improvements as illustrated in FIG. 15.

FIG. 20 is a perspective view of a Yankauer tip.

DETAILED DESCRIPTION OF THE PREFERRED EMBODIMENT

Figure 17:
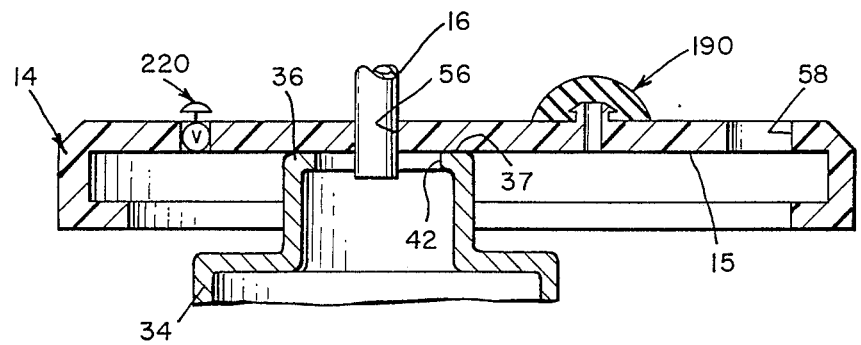
FIG. 17 is an enlarged cross-sectional view of the cap of the aspirator, showing another alternative method by which the bellows cap can be attached to the cap of the aspirator.
Figure 18:
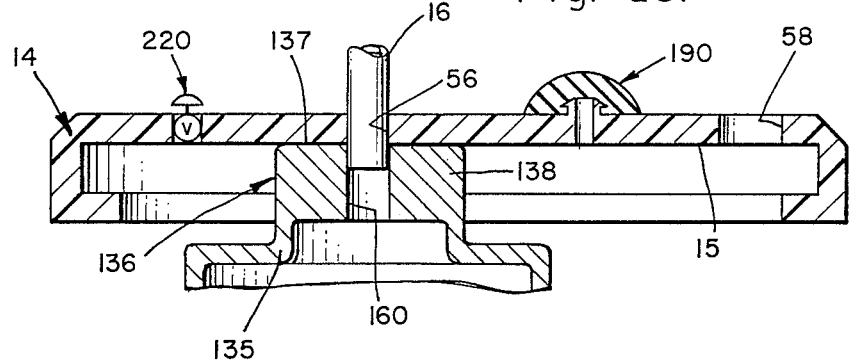
FIG. 18 is an enlarged cross-sectional view of the cap of the aspirator, showing a further alternative method by which the bellows cap can be attached to the cap of the aspirator.

Referring to FIG. 1, there is shown aspirator 10 having a cylindrical container 12, cap 14, suction tube 16, terminating in flared mouthpiece 18 which is a separate piece having nipple 19 which is inserted into suction tube 16, and patient tube 20, terminating in Murphy tip 22, all illustrated in perspective. Murphy tip 22 consists of cutting patient tube 20 at an oblique angle to present a more easily inserted surface, and providing aperture 21 adjacent to the tip, as is well-known in the art.

In the preferred embodiment illustrated in FIG. 1, suction tube 16 and patient tube 20 are made of a flexible, rubber-like material, typically rubber or a synthetic substitute, such as polyvinyl chloride or other material well known in the art. Cylindrical container 12 is preferably made of a hard plastic material, by means of injection or blowmolding, but may be made of any rigid material, such as metal or hard rubber. Aspirator 10 is preferably disposable and is about 5 centimeters in outside diameter and about 10 centimeters long.

In use, aspirator 10 is hung from the user's neck by a cord, so that aspirator 10 is at about mid-chest level, and mouthpiece 18 is inserted into the user's mouth. Murphy tip 22 of patient tube 20 is inserted into the body cavity to be drained, and then the user sucks on flared mouthpiece 18, creating a partial vacuum that is communicated through patient tube 20 to the patient, by means that will be described in greater detail below, thereby drawing liquid and other fluid from the body cavity of the patient. When used as described, aspirator 10 leaves both of the user's hands free, to hold the patient and manipulate patient tube 20. That is, the use of the hands is not required to hold or otherwise manipulate aspirator 10 or mouthpiece 18, a great advantage in using the present invention. When used in this fashion, the preferred length of suction tube 16 is approximately 20 to 30 centimeters, and the preferred length of patient tube 20 is about 30 to 40 centimeters.

Referring to FIG. 2, cylindrical container 12 comprises two internal chambers, vacuum creating chamber 24, and mucus trap 26, created by sidewall 28, and internal upstanding partition 30, which is integrally formed with sidewall 28 of cylindrical container 12 during molding, and is attached to bottom wall 32, as well as two lines of joinder with sidewall 28, as is best illustrated in FIG. 3. Internal upstanding partition 30 rises upward through most of the height of cylindrical container 12, preferably rising a distance within the range of one-third to seven eighths of the length of the container, but does not reach cap 14, thereby creating a path for communication of air and other gaseous fluid between vacuum creating chamber 24 and mucus trap 26.

Vacuum creating chamber 24 contains bellows 34, attached to bellows cap 36 by being integrally formed therewith, or attached by a suitable adhesive. Bellows 34 is preferably made from silicon rubber, having a thickness of from about 1 to about 1.5 millimeters. Silicon rubber is a material well known in the art of medical supplies and is also employed in such well known household items as baby bottle nipples. Silicon rubber has an excellent memory, which consistently restores an article formed from it to its original shape, if it is deformed and then the deforming force is removed. Therefore, no spring or other elastic member is required in bellows 34. Bellows 34 is preferably formed in a single unitary piece, having a sealed bottom 38 formed of the same material, by blow molding.

Referring to FIG. 7, there is most clearly illustrated the relationship between bellows 34, bellows cap 36, bellows stopper 40, and cap 14. Bellows cap 36 may conveniently be formed from hard rubber or the like and attached to the top of bellows 34 with a conventional adhesive. The top of bellows cap 36 comprises aperture 42 for receiving bellows stopper 40, made of pliable rubber or the like, and having a tapered nose section 44, for easing penetration of aperture 42, slot 46, circumferentially disposed about the base of bellows stopper 40, adjacent to tapered nose section 44, for further easing penetration of aperture 42 by bellows stopper 40 into bellows cap 36, and in which top wall 37 of bellows cap 34 is seated when bellows stopper 40 is inserted through aperture 39 of bellows cap 36.

Attached to the top of bellows stopper 40 and integrally formed therewith is nipple 48, for allowing attachment of suction tube 16. Central orifice 50 penetrates the entire length of bellows stopper 40, allowing gaseous communication from suction tube 16 to the interior of bellows 34.

Cap 14 includes depending circumferential skirt portion 52, which terminates in inwardly projecting circumferential lip 54, and includes suction tube aperture 56, and patient tube aperture 58, in its top portion.

Suction tube aperture 56 is penetrated by nipple 48 of bellows stopper 40 until cap 14 is sandwiched between base section 41 and flange 43 of bellows stopper 40. Mouthpiece 18, suction tube 16, bellows stopper 40, and bellows 34 thereby provide a closed system with mouthpiece 18 providing the only means of entry and exit of gas or other fluid into or out of bellows 34.

Several alternative structures for the joining of the bellows cap 36, cap 14 and suction tube 16 is illustrated in FIGS. 15 through 19. In one alternative arrangement, the bellows cap 36 is integrally formed with the inside of cap 14 and aperture 42 in bellows cap 36 is aligned directly with suction tube aperture 56 in cap 14. Referring to FIGS. 15 and 16, one way in which bellows cap 36 may be integrally formed with cap 14 is to have joining member 140 molded into the bottom of cap 14, which joining member 140 includes slot 146 to accommodate aperture 42 of bellows cap 36. Bellows cap 36 is permanently affixed to joining member 140 at the location of slot 146. Joining member 146 may also include an integrally formed nipple 148 which includes suction tube aperture 56 of cap 14 and rises above the top 17 of cap 14 and onto which the suction tube 16 may be placed. The joining member 146 includes a central orifice 56 from suction tube aperture 56 which also extends through the nipple 148, if present. Accordingly, the suction tube 16 rests only on nipple 148 and the flow of air passes from suction tube 16 through aperture 56 into bellows 34 which is attached to bellows cap 36.

Alternatively, the joining member 140 can be eliminated and the top 37 of bellows cap 36 can be affixed directly to the underside 15 of cap 14 such that aperture 42 is aligned with suction tube aperture 56 in cap 14. Suction tube 16 extends through aperture 56 and directly into the bellows cap 36 and bellows 34. This is illustrated in FIG. 17.

In the embodiment in which the joining member is eliminated, the central cap is preferably formed with a more solid interior and only a narrow orifice such that the suction tube 16 extends through suction tube aperture 56 and is aligned with narrower orifice 160. This is illustrated in greater detailed in FIG. 18 in which bellows cap 136 includes a solid interior 138 having central orifice 160 in alignment with suction tube 16. It is also possible for the suction tube 16 to extend into central orifice 160. The solid bellows cap 136 includes side wall 135 which extends directly into the bellows. Bellows cap 136 is attached through its top 137 to the underside 15 of cap 14.

Figure 19:
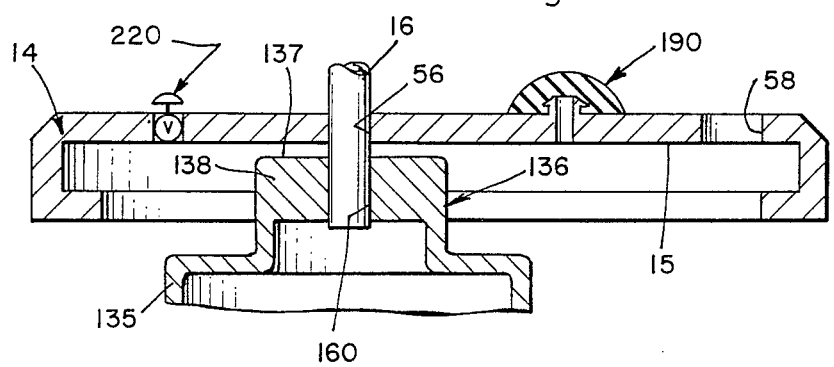
FIG. 19 is an enlarged cross-sectional view of the cap of the aspirator, showing an alternative embodiment of the bellows cap attached directly to the suction tube.

In another variation of this structure, if the press fit between suction tube 16 and the central orifice 160 is very tight, it is possible to have bellows cap 136 be supported directly by the suction tube 16 and the top 137 of bellows cap 136 need not be affixed to the underside 15 of cap 14. This is illustrated in FIG. 19. In this embodiment, suction tube 16 extends well into orifice 160, as illustrated in FIG. 19.

As best illustrated in FIGS. 2, 13, one end of patient tube 20 is disposed downward within mucus trap 26 of aspirator 10, at a distance in the range of about 3 to about 5 centimeters, or about one-third to about three-fourths of the length of the container, thereby insuring that mucus sucked into aspirator 10 falls into mucus trap 26, as long as aspirator 10 is in virtually any orientation other than upside down. Tapered portion 60 of patient tube 20 disposed within container 10 is uniformly tapered along the length intended to remain within aspirator 10, such that the diameter of tapered portion 60 of patient tube 20 is greater than the diameter of patient tube aperture 58.

Operation of aspirator 10 is clearly illustrated in FIGS. 2 and 3. Referring to FIG. 2, bellows 34 is shown in its relaxed state. When a user sucks on mouthpiece 18, bellows 34 is contracted by air pressure conducted through patient tube 20, into the interior of aspirator 10, through mucus trap 26, over internal upstanding partition 30, and into vacuum creating chamber 24, allowing bellows 34 to contract. Naturally, as bellows 34 contracts, air is drawn into aspirator 10. When Murphy tip 22 of patient tube 20 is lodged near or in mucus or other bodily fluids, these liquids and other fluids are drawn into mucus trap 26. Liquid falls to the bottom of mucus trap 26, while gas flows into vacuum creating chamber 24. Referring to FIG. 6, bellows 34 is illustrated in its contracted, or vacuum creating, state.

Naturally, when the medical care provider releases the sucking action from the mouthpiece 18, bellows 34 expands to its original position, as illustrated in FIG. 2 and FIG. 15, due to the memory of the silicon rubber material the bellows is made from. Expansion of bellows 34 naturally expels air from vacuum creating chamber 24, which can only be exhausted from aspirator 10 through patient tube 20. It has been found in practice that one suction cycle is usually sufficient to withdraw mucus and other liquids from the pertinent body cavity. If, however, more than one suction cycle is required, it has been found that allowing the air to be blown out through patient tube 20 into the body cavity being drained does not create any problems or difficulties. Hence, there is no real need for any type of valves that would prevent air from being blown out through patient tube 20.

Referring to FIG. 4, there is shown a plan view of aspirator 10 according to the present invention. Such an aspirator may include a straight line internal upstanding partition 30, as illustrated in FIGS. 2 and 3, or it may include an arcuate internal upstanding partition 62, as illustrated in FIG. 5, which better utilizes interior volume of aspirator 10, by allowing partition 62 to be closer to bellows 34, thereby allowing use of a smaller diameter cylindrical container 12.

Several enhancements for providing safer and more efficient operation are shown in FIGS. 14, 15 and 16. One such enhancement for safer utilization of the present invention is to provide a moisture trap 180 inside the suction tube 16 which acts as a moisture block. This is illustrated in FIG. 15. The moisture trap 180 is a filter which permits air to pass when it is dry but if moisture is present, the filter swells up and occludes the passageway in suction tube 16, preventing air from passing. This is a valuable safety enhancement in the event the bellows or other sealing arrangement should break and moisture from the sucked contents of the baby's stomach enter the suction system. By providing this occlusion, the possibility of the person working the apparatus sucking in such material or sucking in contaminated air is significantly reduced.

Referring to FIGS. 14 through 16, a further enhancement for more efficient operation of the present invention is the inclusion of an injection port 190 located in the area where mucus is collected, for example in the cap 14 immediately above the mucus trap 26 area of the present invention aspirator. The injection port 190 includes an opening 192 in the cap 14, and having a structural support member 194 extending through the opening 192 and which supports a diaphragm 196. After the mucus is collected, instead of opening the cap 14 to remove the mucus, the laboratory technician can place the needle of a syringe through the membrane 196, through opening 192 and into the mucus trap 26 area and draw out the mucus into the syringe, thereby eliminating the possibility of coming in direct conduct with contaminated mucus.

Referring to FIG. 14, an additional enhancement is the inclusion of a clip 200 which includes an internal tapered opening 202. The clip 200 is placed around the patient tube 20 in an area between the cap 14 and the tip 22. During operation, the wider portion 204 of opening 202 surrounds the patient tube 20 so that the patient tube 20 is unobstructed. After the mucus has been sucked out of the baby and is in the mucus trap 26, the clip 200 is slid so that its narrower portion 206 surrounds and pinches in the patient tube 20, to thereby occlude flow of liquid after the suction process is completed, thereby further assuring that no mucus can flow out of the patient tube and back into the patient.

The invention may also include means for releasing air from the container during the relaxation cycle of the bellows, that is, means for permitting air to be exhausted from the container while the bellows expand without having the displaced air exhausted through the patient tube. Referring to FIGS. 14 through 16, this air releasing means 220 may be a spring loaded valve 222 fit inside an aperture 210 in the top 14 (or it may be in the sidewall 12) of the container. The valve 222 is normally closed so no air can enter the container or escape from the container through this aperture 210. When a push button 224 or similar release mechanism connected to the valve 222 is activated, the valve 222 opens to let air escape from the chamber, thereby depressurizing the entire container so the bellows 34 can expand to its equilibrium position much more rapidly without the possibility of air or liquid being pushed up the patient tube 20 and back into the patient's stomach.

Referring to FIG. 20, an additional improvement in the present invention is to include a Yankauer suction tip 230 at the end of the patient tube so that the apparatus may be switched from patient to patient by replacement of the Yankauer tip 230. In this way, the entire apparatus can remain in use and only the Yankauer tip 230 changed when a new patient is worked on. This is especially useful in battlefield conditions where the present invention aspirator may be used to remove mucus and other debris from the mouth of a wounded soldier. Due to the extreme conditions of battle, it is easier to maintain the same apparatus and merely switch the patient tube tip when treating many different wounded soldiers.

Referring to FIG. 8, there is shown an alternative embodiment of aspirator 11 having separate vacuum creating chamber 70, including suction tube aperture 72, and mucus trap 74, including patient tube aperture 76. Vacuum creating chamber 70 having cap 71 and mucus trap 74 having cap 75 are joined by sidewalls 78, 80, which are both tangent to the cross-sectional circles of vacuum creating chamber 70 and mucus trap 74. Internal upstanding partition 82 isolates mucus and other bodily liquids in mucus trap 74 from contact with vacuum creating chamber 70, but does not reach to the top of aspirator 11, as was described in conjunction with FIGS. 1 through 7 above. Sidewalls 78, 80 include frangible score line 84, allowing aspirator 11 to be cleanly and easily broken along frangible score line 84, thereby separating mucus trap 74 from vacuum creating chamber 70, providing a smaller container for use in analysis of the mucus or other bodily liquid trapped in mucus trap 74.

Referring to FIGS. 10 and 11, there is shown another alternative embodiment of aspirator 10 according to the present invention, in which vacuum creating chamber 70 is a cylindrical container wholly separate from mucus trap 74, which are joined together by rubber band 86, or other suitable fastener. Tube 94 connects vacuum chamber 70 and mucus trap 74. Tube 94 is disposed outside aspirator 13 across the top of aspirator 13, which includes a separate vacuum chamber cap 88, and a separate mucus trap cap 98, each of which may be removable. Tube 94 may be inserted into aperture 91 of cap 88, and aperture 93 of cap 98. Alternatively, of course, nipples may be integrally formed in caps 88, 98 to receive tube 94.

A suction tube (not shown) may be attached at suction tube aperture 89 by any convenient means, such as those described above. A patient tube may be conveniently attached as described with reference to FIGS. 1-7 through patient tube aperture 90. In the embodiment illustrated in FIGS. 10, 11, vacuum chamber cap 88 is not removable, but it may be a removable cap like that of FIG. 7 if desired.

The embodiment illustrated in FIGS. 10, 11 allows easy and quick separation of vacuum creating chamber 70 from mucus trap 74, by removing rubber band 86 and removing the tube 94 from aperture 93. Mucus trap 74 can then be sealed by inserting a small stopper into each aperture of cap 98, and sent to the laboratory, where the contents can be analyzed to determine the cause of any medical problems the patient may be suffering. Mucus trap 74 of this embodiment has a separate mucus trap cap 98, having the depending circumferential skirt and inwardly projecting lip which allows mucus trap cap 98 to be removed from mucus trap 74 easily, as illustrated in FIG. 7. In other respects, especially regarding the bellows vacuum and fluid separation system described above, the embodiment of FIGS. 10, 11 operates the same as that shown and described in reference to FIGS. 1-7.

The embodiment illustrated in FIG. 10 is particularly preferred because it allows re-use of vacuum creating chamber 70 and bellows 34, which are the most expensive components of the system, while at the same time maintaining the separation of patient fluids from the medical care provider. If desired, aspirator 10 can be sterilized, particularly vacuum creating chamber 70, which will prevent spread of infection from one patient to another if the device is re-used.

In its preferred embodiment, however, aspirator 10 is disposable, and furthermore is sterile when shipped and is protected by sterile wrapping, thus insuring that bacteria or germs cultured from mucus trapped in mucus trap 74 is from the patient.

Referring to FIG. 12, there is illustrated suction tube 16, including flared mouthpiece 18 having nipple 19 for insertion into tube 16. Referring to FIG. 13, there is illustrated patient tube 20, including Murphy tip 22 having aperture 21, and tapered portion 60 for insertion upwardly through cap 14, or other cap or closure on mucus trap 26, 74, and so forth.

Of course, the present invention is not intended to be restricted to any particular form or arrangement, or any specific embodiment disclosed herein, or any specific use, since the present invention may be modified in various particulars or relations without departing from the scope of the claimed invention shown and described herein, of which the apparatus shown are intended only for illustration and for disclosure of operative embodiments and not to show all of the various forms or modifications which might embody the invention.

The invention has been described in considerable detail in order to comply with the patent laws by providing a full public disclosure of one of its forms. Such detailed description is not, however, intended in any way to limit the broad features or principles of the invention, or the scope of the patent property to be granted.

WHAT IS CLAIMED IS:

1. An aspirator for removing bodily fluids through human suction and subsequent collection of the removed bodily fluids, comprising:
   a. a container having a bottom wall and a side wall;
   b. a top having a first aperture therein and a second aperture therein spaced apart from the first aperture, the top being removably attached to said container;
   c. said container further comprising an upstanding partition within said container to divide the container into a first chamber and a second chamber;
   d. said upstanding partition extending from the bottom of said container to a distance between the bottom of said container and said top to create a division opening between said first and second chambers to thereby permit gaseous communication but not liquid communication between said first and second chambers;
   e. said first aperture opening into said first chamber and said second aperture opening into said second chamber;
   f. a first hollow tube having two ends, with the first end inserted through said first aperture such that said first hollow tube extends for a distance below said division opening and into said first chamber for a total distance inside the container in the range from about one-third to about three-fourths of the length of the container and said second end extends for a distance beyond said top and further comprises at least one opening adjacent its tip;
   g. a flexible bellows member comprising an integrally formed flexible bellows and terminating in a sealed bottom at one end and affixed to a bellows cap at its other end;
   h. said bellows cap having an opening extending into the bellows and attached to the top of said container such that the opening in the bellows cap is aligned with said second aperture in the top of the container;
   i. the top of said container further comprising means for receiving a hollow tube in alignment with said second opening, the means comprising a central opening for fluid communication with the second aperture and bellows;
   j. a second hollow tube having two ends, with the first end attached to said means for receiving a hollow tube aligned with said second opening and the second end attached to a mouthpiece, to thereby provide a closed system permitting gaseous communication between the mouthpiece, the second hollow tube, the bellows cap and the bellows; and
   k. said flexible bellows extending into said second chamber for a distance beyond said division opening such that the flexible bellows is in its fully expanded position when in its equilibrium state;
   l. whereby in use, the second end of said first hollow tube is inserted into the patient from which bodily fluid is to be removed and the mouthpiece of the second hollow tube is sucked on by the person treating the patient, and suction through the mouthpiece will cause said flexible bellows to contract to thereby create a vacuum in said second chamber which through gaseous communication with said first chamber causes air and bodily fluids from the patient to be sucked into and remain in the first chamber while the airtight system from the mouthpiece through the flexible bellows prevents any direct communication of air or bodily fluids between the patient and the person treating the patient.

2. An aspirator in accordance with claim 1, wherein:
   a. the top of said container further comprises a joining member attached to the underside of said top and extending into the second chamber, and further including a slot therein;
   b. the means for receiving a hollow tube is a nipple extending out of the upper surface of the top of the container; and
   c. the opening in said bellows cap is attached to the joining member at the location of the slot.

3. An aspirator in accordance with claim 1 wherein said top of said bellows cap is attached to the underside of the top of said container.

4. An aspirator in accordance with claim 1 further comprising an injection port including a diaphragm through which a syringe can be inserted to remove mucus from the container.

5. An aspirator in accordance with claim 1 further comprising a pressure relief valve which is normally closed and which may be activated to be opened to permit air to escape from the container as the flexible bellows expands to its equilibrium state.

6. An aspirator in accordance with claim 1 wherein said second hollow tube further comprises a moisture trap wherein gaseous flow is occluded between the mouthpiece and the container in the event moisture enters the second hollow tube.

7. An aspirator in accordance with claim 1 wherein said first hollow tube further comprises a clip by which fluid flow through the first hollow tube may be occluded.

8. An aspirator in accordance with claim 1 wherein the second end of said first hollow tube further comprises a removable suction tip.

9. An aspirator for removing bodily fluids through human suction and subsequent collection of the removed bodily fluids, comprising:
   a. a container having a bottom wall and a side wall;
   b. a top having a first aperture therein and a second aperture therein spaced apart from the first aperture, the top being removably attached to said container;
   c. said container further comprising an upstanding partition within said container to divide the container into a first chamber and a second chamber;
   d. said upstanding partition extending from the bottom of said container to a distance between the bottom of said container and said top to create a division opening between said first and second chambers to thereby permit gaseous communication but not liquid communication between said first and second chambers;
   e. said first aperture opening into said first chamber and said second aperture opening into said second chamber;
   f. a first hollow tube having two ends, with the first end inserted through said first aperture such that said first hollow tube extends for a distance below said division opening and into said first chamber for a total distance inside the container in the range from about one-third to about three-fourths of the length of the container and said second end extends for a distance beyond said top and further comprises at least one opening adjacent its tip;

g. a flexible bellows member comprising an integrally formed flexible bellows and terminating in a sealed bottom at one end and affixed to a bellows cap at its other end;

h. said bellows cap having an opening extending into the bellows and attached to the top of said container such that the opening in the bellows cap is aligned with said second aperture in the top of the container;

i. said top of said bellows cap is attached to the underside of the top of said container;

j. a second hollow tube having two ends, with the first end extending through said second aperture in the top of the container, and the second end attached to a mouthpiece, to thereby provide a closed system permitting gaseous communication between the mouthpiece, the second hollow tube, the bellows cap and the bellows; and k. said flexible bellows extending into said second chamber for a distance beyond said division opening such that the flexible bellows is in its fully expanded position when in its equilibrium state;

l. whereby in use, the second end of said first hollow tube is inserted into the patient from which bodily fluid is to be removed and the mouthpiece of the second hollow tube is sucked on by the person treating the patient, and suction through the mouthpiece will cause said flexible bellows to contract to thereby create a vacuum in said second chamber which through gaseous communication with said first chamber causes air and bodily fluids from the patient to be sucked into and remain in the first chamber while the airtight system from the mouthpiece through the flexible bellows prevents any direct communication of air or bodily fluids between the patient and the person treating the patient.

10. An aspirator in accordance with claim 9 further comprising an injection port including a diaphragm through which a syringe can be inserted to remove mucus from the container.

11. An aspirator in accordance with claim 9 further comprising a pressure relief valve which is normally closed and which may be activated to be opened to permit air to escape from the container as the flexible bellows expands to its equilibrium state.

12. An aspirator in accordance with claim 9 wherein said second hollow tube further comprises a moisture trap wherein gaseous flow is occluded between the mouthpiece and the container in the event moisture enters the second hollow tube.

13. An aspirator in accordance with claim 9 wherein said first hollow tube further comprises a clip by which fluid flow through the first hollow tube may be occluded.

14. An aspirator in accordance with claim 9 wherein the second end of said first hollow tube further comprises a removable suction tip.

15. An aspirator for removing bodily fluids through human suction and subsequent collection of the removed bodily fluids, comprising:

a. a container having a bottom wall and a side wall;

b. a top having a first aperture therein and a second aperture therein spaced apart from the first aperture the top being removably attached to said container;

c. said container further comprising an upstanding partition within said container to divide the container into a first chamber and a second chamber;

d. said upstanding partition extending from the bottom of said container to a distance between the bottom of said container and said top to create a division opening between said first and second chambers to thereby permit gaseous communication but not liquid communication between said first and second chambers;

e. said first aperture opening into said first chamber and said second aperture opening into said second chamber;

f. a first hollow tube having two ends, with the first end inserted through said first aperture such that said first hollow tube extends for a distance below said division opening and into said first chamber for a total distance inside the container in the range from about one-third to about three-fourths of the length of the container and said second end extends for a distance beyond said top and further comprises at least one opening adjacent its tip;

g. a flexible bellows member comprising an integrally formed flexible bellows and terminating in a sealed bottom at one end and affixed to a bellows cap at its other end;

h. said bellows cap including a solid interior having an opening therethrough which extends into the bellows;

i. a second hollow tube having two ends, with the first end extending through said second aperture in the top of the container and into the opening in said bellows cap to form a press fit against the solid interior of the bellows cap and thereby support the bellows cap and flexible bellows, and the second end attached to a mouthpiece, to thereby provide a closed system permitting gaseous communication between the mouthpiece, the second hollow tube, the bellows cap and the bellows; and j. said flexible bellows extending into said second chamber for a distance beyond said division opening such that the flexible bellows is in its fully expanded position when in its equilibrium state;

k. whereby in use, the second end of said first hollow tube is inserted into the patient from which bodily fluid is to be removed and the mouthpiece of the second hollow tube is sucked on by the person treating the patient, and suction through the mouthpiece will cause said flexible bellows to contract to thereby create a vacuum in said second chamber which through gaseous communication with said first chamber causes air and bodily fluids from the patient to be sucked into and remain in the first chamber while the airtight system from the mouthpiece through the flexible bellows prevents any direct communication of air or bodily fluids between the patient and the person treating the patient.

16. An aspirator in accordance with claim 15 wherein said top of said bellows cap is attached to the underside of the top of said container.

17. An aspirator in accordance with claim 15 further comprising an injection port including a diaphragm through which a syringe can be inserted to remove mucus from the container.

18. An aspirator in accordance with claim 15 further comprising a pressure relief valve which is normally closed and which may be activated to be opened to permit air to escape from the container as the flexible bellows expands to its equilibrium state.

19. An aspirator in accordance with claim 15 wherein said second hollow tube further comprises a moisture trap wherein gaseous flow is occluded between the mouthpiece and the container in the event moisture enters the second hollow tube.

20. An aspirator in accordance with claim 15 wherein said first hollow tube further comprises a clip by which fluid flow through the first hollow tube may be occluded.

21. An aspirator in accordance with claim 15 wherein the second end of said first hollow tube further comprises a removable suction tip.

* * * * *